United States Patent [19]

Toscano

[11] Patent Number: 4,673,736

[45] Date of Patent: Jun. 16, 1987

[54] PROCESS FOR THE PREPARATION OF (8S)-8-FLUOROERYTHROMYCINS

[75] Inventor: Luciano Toscano, Milan, Italy

[73] Assignee: Pierrel SpA, Naples, Italy

[21] Appl. No.: 629,768

[22] Filed: Jul. 11, 1984

[30] Foreign Application Priority Data

Jul. 18, 1983 [IT] Italy .............................. 22104 A/83

[51] Int. Cl.⁴ ........................ C07H 1/00; C07H 17/08
[52] U.S. Cl. ....................................... 536/7.2; 536/7.5
[58] Field of Search ........................................ 536/7.2

[56] References Cited

U.S. PATENT DOCUMENTS 4,514,562  4/1985  Toscano .............................. 536/7.2

FOREIGN PATENT DOCUMENTS 0056291  7/1982  European Pat. Off. ............. 536/7.2
0080763  6/1983  European Pat. Off. ............. 536/7.2

*Primary Examiner*—Johnnie R. Brown
*Attorney, Agent, or Firm*—Murray and Whisehunt

[57] ABSTRACT

For the synthesis of (8S)-8-fluoroerythromycins the corresponding 8,9-anhydroerythromycins 6,9-hemiketal are directly fluorinated with perchloryl fluoride.

10 Claims, No Drawings

PROCESS FOR THE PREPARATION OF (8S)-8-FLUOROERYTHROMYCINS

The present invention relates to a process for the synthesis of (8S)-8-fluoroerythromcyins, having the general formula:

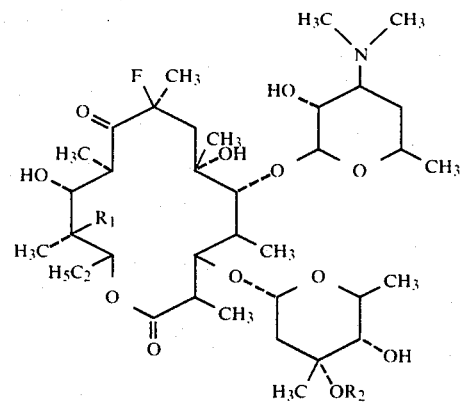

representing:

|  | R₁ | R₂ |
| --- | --- | --- |
| (8S)-8-fluoroerythromycin A | for OH | CH₃ |
| (8S)-8-fluoroerythromycin B | for H | CH₃ |
| (8S)-8-fluoroerythromycin C | for OH | H |
| (8S)-8-fluoroerythromycin D | for H | H | useful as antibacterial agents.

The subject macrolide antibiotics have been already described in European Patent Applications Nos. 822019.6 and 82201476.7.

In the first Application a microbiological process is disclosed for their preparation, based on the use of blocked mutants of the S.erythraeus species and of a monofluorinated substrate. Starting for example from (8S)-8-fluoroerythronolide A, in addition to (8S)-8-fluoroerythromycin A about 50% of (8S)-8-fluoroery- thromycin C is also formed, hence the final yeld of each antibiotic is relevantly lowered.

Such a case is represented in the following scheme I

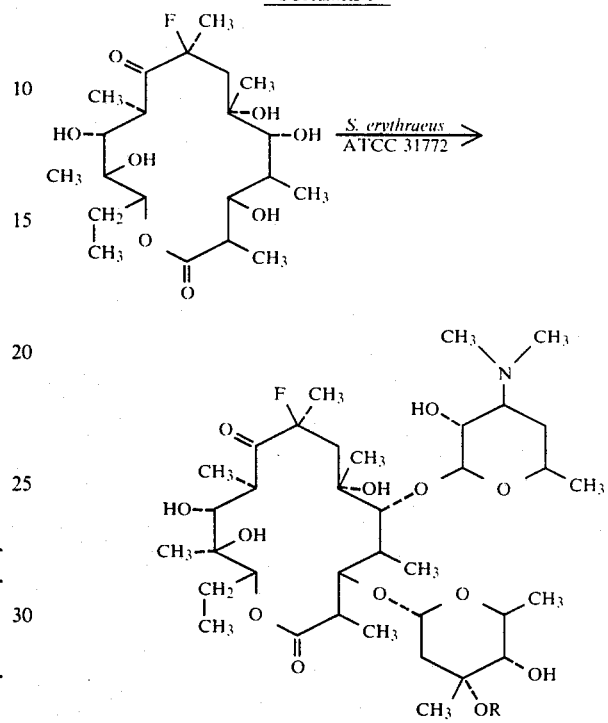

R = CH₃(8S)—8-fluoroerythromycin A
R = H(8S)—8-fluoroerythromycin C

In the second afore mentioned European Application a process is disclosed and claimed for the synthesis of the subject antibiotics.

With specific reference to (8S)-8-fluoroerythromycin A, the following scheme (II) illustrates such a synthesis process:

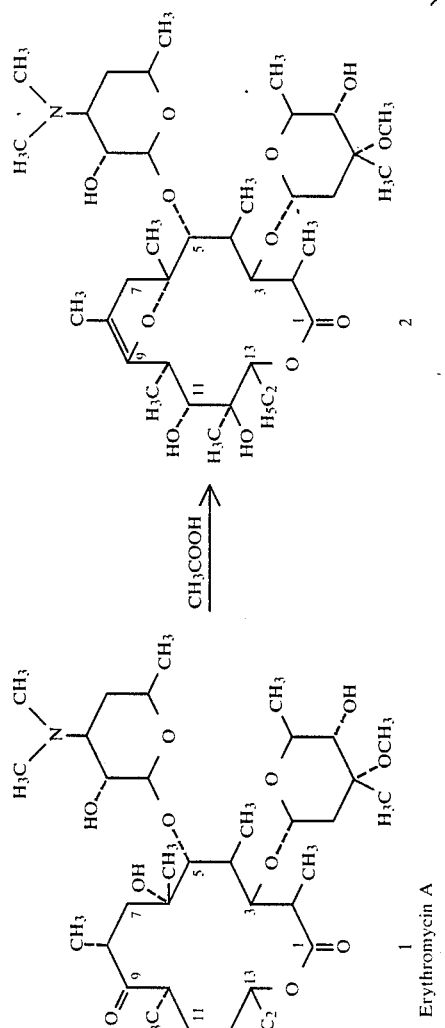

According to such a synthesis an enol-ether function (2) is generated in the molecule of erythromycin A (1) and subsequently the N-dimethyl group of desosamine is protected as N-oxide (3) to avoid the partial or total N-demethylation of the basic sugar during the fluorination; fluorination of (3) with trifluoromethyl hypofluorite or perchloryl fluoride, followed by hydrogenolysis, gives (8S)-8-fluoroerythromycin A (5). As a matter of fact, by operating according to the disclosure of the second Application erythromycin A can be converted into (8S)-8-fluoroerythromycin A, with a yield of about 35% in four subsequent steps (scheme II):

erythromycin A (1)→8,9-anhydroerythromycin A
6,9-hemiketal (2)→8,9-anhydroerythromycin A
6,9-hemiketal N-oxide
(3)→(8S)-8-fluoroerythromycin A N-oxide
(4)→(8S)-8-fluoroerythromycin A (5)

The process of the afore mentioned second patent application does also contemplate as an alternative (indicated as "route b" in the specification) the fluorination of the compound (2), with a partial demethylation of the desosamine, followed by a methylation having the purpose of restoring the N-dimethyl group of the basic sugar.

For this emboidment the use of a fluoroxyperfluoroalkane, particularly fluoroxytrifluoromethane, or of perchloryl fluoride is also foreseen as a reactant capable of generating electrophilic fluroine.

In the aforesaid European Application No. 82001476.7 examples are also reported illustrating how such a synthesis pattern ("route b") is punctually confirmed by the practical results in the case of the fluoroxytrifluoromethane, whereby on the basis of the behaviour analogy of perchloryl fluoride in the other route it was reasonably to be presumed that also for route b the synthesis using perchloryl fluoride would follow the same pattern found with the fluoroxytrifluoromethane.

It is obvious that whatever simplification of a chemical synthesis and/or increase in yields constitute highly desirable objectives from the industrial point of view, especially in the case of antibiotics the production of which must take place in substantial amounts.

It has been now surprisingly found and is the subject of the present invention that the perchloryl fluoride has a different behaviour, which might not be foreseen from experience with the other fluorinating agents considered in the above cited European Applications.

Consequently according to the present invention a process is provided for the synthesis of a (8S)-8-fluoroerythromycin, characterized in that 8,9-anhydroerythromycin 6,9-hemiketal is directly converted to the corresponding (8S)-8-fluoroerythromycin through fluorination with perchloryl fluoride as the fluorinating agent.

Otherwise stated, the process of the present invention permits erythromycin (or the derivative thereof 8,9-anhydroerythromycin 6,9-hemiketal) to be directly converted into (8S)-8-fluorerythromycin without it being necessary to protect the N-dimethyl group of the desosamine during the fluorination and without the necessity of carrying out a subsequent step of methylating hydrogenation, which is foreseen in European Application No. 82201476.7.

Another important feature of the present invention resides in that the final yield of (8S)-8-fluoroerythromycin is increased to values of at least 70%, it possibly achieving even 100%, always in weight terms.

The carrying out of the process of the invention, is illustrated by the following scheme (III):

SCHEME III

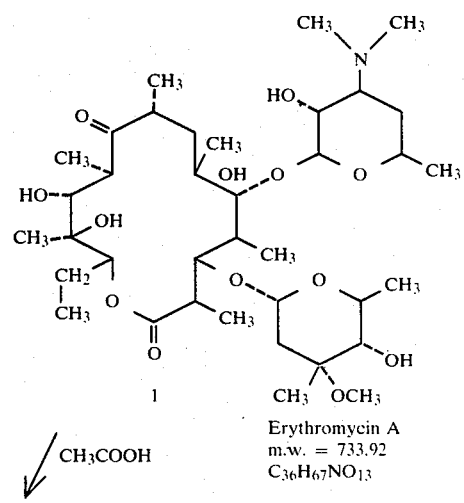

Erythromycin A
m.w. = 733.92
$C_{36}H_{67}NO_{13}$

-continued
SCHEME III

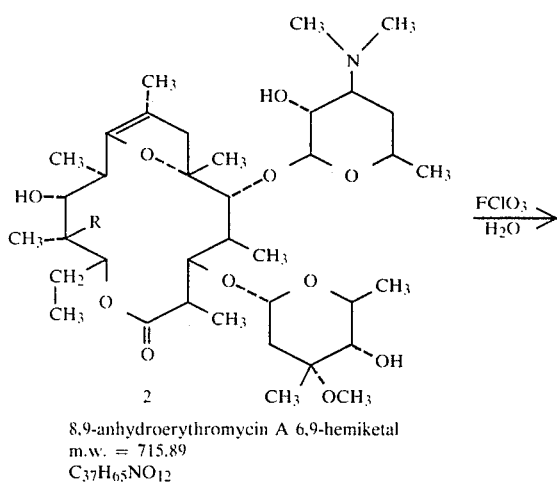

8,9-anhydroerythromycin A 6,9-hemiketal
m.w. = 715.89
C_{37}H_{65}NO_{12}

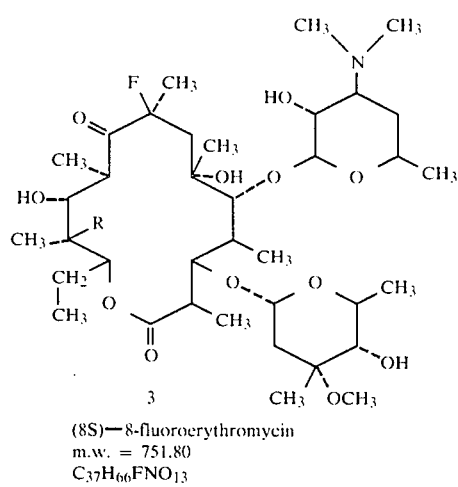

(8S)—8-fluoroerythromycin
m.w. = 751.80
C_{37}H_{66}FNO_{13}

Erythromycin A (1), dissolved in glacial acetic acid at room temperature for 2 hours, is readily converted into 8,9-anhydroerythromycin A 6,9-hemiketal (2). The acetic solution is adjusted to pH 4.2 by means of 32% KOH solution and then diluted with water-tetrahydrofuran. The fluorinating gas, perchloryl fluoride, is bubbled through the reaction mixture up to disappearance of the starting product (2), (8,9-anhydroerythromycin A 6,9-hemiketal) or is allowed to be slowly absorbed "by contact". Among the reaction solvents, besides tetrahydrofuran also pyridine, dioxane and their mixtures are contemplated. When the acetic solution is diluted with water-pyridine (in volumes equal to that of acetic acid) no need exists of using the 32% KOH solution to adjust the pH to 4.2. The presence of water in the reaction mixture is indispensable in order to obtain high final yields of (8S)-8-fluoroerythromycin A (3). It is preferable to carry out the reaction at low temperatures, preferably in the range of ±5° C., and at a pH of between 4 and 7.

The invention shall be now illustrated, in a non limiting sense, by the following examples.

EXAMPLE 1

In a glass reactor of about 3 litre capacity, 100 g (0.136 moles) of erythromycin A (m.w. 733.92) are dissolved in 400 ml of glacial acetic acid at 20° C. The solution is allowed to stand at this temperature for 2 hours by monitoring the reaction by HPLC (high pressure liquid chromatography).

When the reaction is completed, the pH is corrected to 4.3 with 32% KOH (about 250 ml), by maintaining the temperature at 20° C.

Then water (400 ml) and tetrahydrofuran (1000 ml), free of peroxides, are added.

The solution is cooled to 0° C. and the addition of perchloryl fluoride (21.4 g corresponding 0.209 moles) is slowly started through a gas sparger. The reaction mixture is maintained at 0° C. and the reaction is monitored by HPLC.

The reaction should be completed in about 1 hour; in the contrary case further perchloryl chloride is slowly added at 0° C. The reactor temperature is brought again to 20° C. and the possible excess of perchloryl chloride is removed by blowing nitrogen. By maintaining the temperature at 20° C. the pH is adjusted to 7.2 with 32% KOH (about 950 ml) and the reaction mixture is concentrated under vacuum, at a maximum temperature of 40° C., until a volume of 2,000 ml is attained.

The pH is then brought to 9 by means of 32% KOH (about 20 ml) and 2000 ml of methylene chloride are added to the reaction mixture. The latter is vigorously stirred for 15 minutes and then the phases are decanted. The organic phase is separated, and washed with a saturated solution of NaCl.

The aqueous phase is extracted two further times with methylene chloride (2000 ml × 2) and these organic phases are also washed with the aforesaid saturated solution of NaCl.

The three chloromethylenic extracts, upon being combined, are dried on anhydrous sodium sulphate.

After filtration the organic phase is concentrated under vacuum at a maximum temperature of 50° C. Absolute ethanol (1000 ml) is added and concentration is continued to 400 ml, this operation being then repeated two further times.

After standing at 0° C. for one night, the product is filtered under vacuum and washed with a small volume of absolute ethanol.

Upon drying to constant weight at 50° C. under vacuum 63.3 g of product are obtained, having the following analytical data:

m.p. 184–5° C.

$[\alpha]_D^{20}$ 31 56.5°(C=1 in methanol).

UV (methanol) 286 nm ($\epsilon$10.9).

IR (KBr) 3520, 3480 (shoulder), 3250, (broad), 1735, 1720, 1460, 1425, 1400, 1380, 1345,1330, 1305, 1280, 1190, 1170,1120, 1090, 1075, 1055, 1030, 1015, 1005,980,960 (shoulder), 935,890,870,855,835,800 cm$^1$.

The elemental anaylsis for $C_{37}H_{66}FNO_{13}$ gave the following values: calculated (%): C 59.10;H 8.85;F 2.52; N 1.86. found (%): C 58.398;H 9.06;F 2.62;N1.92.

The mother liquors together with the washing waters are concentrated under vacuum to give a second crop of product.

The latter, although less pure than the first one, may be qualitatively improved and brought to a purity degree identical to that of the first produced crop through a subsequent crystallization from absolute ethanol.

The second crop (6.7 g) is dissolved in about 20 ml of methylene chloride (recovered from the preceeding concentration) and azeotroped three times with absolute ethanol (3×50 ml, recovered from the preceeding concentration).

After standing overnight at 0° C., the mixture is filtered under vacuum. Then it is washed with a small volume of absolute ethanol and dried to constant weight at 50° C. under vacuum (5.4 g).

The analytical data of the obtained product are like those indicated for the first one.

EXAMPLE 2

In a 1000 litre stainless steel reactor 20 kg (27.25 moles) of erythromycin A are dissolved in 80 litres of glacial acetic acid at 20° C. The solution is allowed to stand at this temperature for 2 hours, the reaction being monitored by HPLC. When the reaction is completed the pH of the reaction mixture is adjusted to 4.3 with 32% KOH (about 50 litres), the temperature being maintained at 20° C. 80 litres of water and 200 litres of tetrahydrofuran (free from peroxides) are added, and then the solution is cooled to 0° C. and a partial vacuum is established in the reactor until an internal pressure of 210 mm Hg is obtained. Then the addition of perchloryl fluoride is started by bubbling the gas until atmospheric pressure is again established in the reactor.

As the reaction proceeds, the pressure of perchloryl fluoride in the vapor phase decreases and when the pressure is reduced to about 525 mm Hg, further perchloryl fluoride is added until atmospheric pressure is restored.

The rection mixture is maintained at 0° C. until the pressure of the vapor phase is reduced to about 210 mm Hg.

The reaction is monitored through HPLC and it should be completed within about 20 hours with a consumption of 28.30 moles. In the case of incomplete reaction further perchloryl fluoride is added at 0° C.

Nitrogen is blown into the reactor, for one hour, in order to eliminate the residual perchloryl fluoride.

Then, the temperature is brought to 20° C., and the pH is adjusted to 7.2 by means of 32% KOH (about 190 litres).

The mixture is concentrated under vacuum at a maximum temperature of 40° C., until a volume of 400 litres is obtained.

The pH is adjusted to 9 with 32% KOH.

Further 400 litres of methylene choride are added to the reaction mixture, which is then vigorously stirred and thereafter the phases are decanted.

The organic phase is separated and washed with a saturated solution of NaCl, taking care of saving the washing waters for the washing of the further subsequent organic phases.

The aqueous phase is extracted two further times with methylene chloride (400 lt×2) and the organic phases are washed with the aforesaid saturated solution of NaCl.

The three combined chloromethylenic extracts are dried on anhydrous sodium sulfate, filtered and the organic phase is concentrated under vacuum at a maximum temperature of 50° C. until a volume of 80 litres is attained.

200 litres of absolute ethanol are added and the mixture is concentrated under vacuum, at a maximum temperature of 50° C., until a volume of 80 litres is obtained, the same operation being then repeated two further times.

After standing overnight at 0° C., the product is centrifuged and washed with a small volume of absolute ethanol.

Thereafter the product is dried at 50° C. under vacuum to constant weight. 13.4 kg of (8S)-8-fluorerythromycin A are obtained having the following analytical data:

m.p. 183–4° C.
$[\alpha]_D^{20}$ −56.2°(C=1 in methanol)
UV (methanol) 286 nm ($\epsilon$9.8)
IR (KBr) 3520, 3480 (shoulder), 3250 (broad), 1735, 1720, 1460, 1425, 1400, 1380, 1345, 1330, 1305, 1280, 1190, 1170, 1120, 1090, 1075, 1055, 1030, 1015, 1005, 980, 960, (shoulder), 935, 890, 870, 855, 835, 800 cm$^{-1}$.

The elemental analysis for $C_{37}H_{66}FNO_{13}$ gave the following values: caluclated (%): C 59.10;H 8.85;F 2.52;N 1.86. found (%): C 59.29;H 9.01;F 2.59;N 1.90.

The mother liquors, together with the washings, are concentrated under vacuum to give a second crop of product.

This second crop although less pure than the first one, can be qualitatively improved and brought to a purity degree identical to that of the firstly obtained product, through a subsequent crystallization from absolute ethanol: in particular the 1st produced crop (1.3 kg) is dissolved in about 4 litres of methylene chloride recovered from the preceeding concentration and azetrope three times with absolute ethanol (3×10 litres) recovered from the preceeding concentration.

After standing overnight at 0° C., the product is filtered on paper using a Buckner.

After washing with a small volume of absolute ethanol, the product is dried at 50° C. under vacuum until a constant weight is obtained (1.1 kg).

The analytical data of this product are similar to those reported for the firstly obtained product. As already mentioned, the preceeding specification and examples specifically refers to (8S)-8-fluoroerythromycin A, but the process of the invention is identically applicable to the other erythromycins and thus to the preparation of the corresponding (8S)-8-flouroerythromycins.

What is claimed is:

1. A process for preparing (8S)-8-fluoroerythromycin having the formula wherein $R_1$ is selected from the group consisting of hydrogen and hydroxy and $R_2$ is selected from the group consisting of hydrogen and methyl, said process comprising fluorinating in one step an acetic solution of the corresponding 8,9-anhydroerythromycin 6, 9-hemiketal having an unprotected N-dimethyl group with perchloryl fluoride, said acetic solution being diluted with water and an inert solvent selected from tetrahydrofuran, pyridine and dioxane, said fluorination being carried out at a temperature of between about −5° C. and +50° C. and at a pH 4 to 7 to directly convert said hemiketal into said (8S)-8-fluoroerythromycin.

2. A process according to claim 1, wherein said temperature is about 5° C.

3. A process according to claim 1, wherein said temperature is about 0° C.

4. A process according to claim 1, wherein said fluorination is carried out by bubbling said perchloryl fluoride through said acetic solution of 8,9-anhydroerythromycin 6,9-hemiketal diluted with water-tetrahydrofuran or water-pyridine.

5. A process according to claim 1, wherein said fluorination is carried out at a pH of about 4.2.

6. A process according to claim 1, wherein said fluorination is carried out by reacting said perchloryl fluoride with said acetic solution of said 8,9-anhydroerythromycin 6,9-hemiketal.

7. A process according to claim 1, wherein $R_1$ is hydroxy and $R_2$ is methyl.

8. A process according to claim 1, wherein $R_1$ is hydrogen and $R_2$ is methyl.

9. A process according to claim 1, wherein $R_1$ is hydroxy and $R_2$ is hydrogen.

10. A process according to claim 1, wherein $R_1$ is hydrogen and $R_2$ is hydrogen.

* * * * *